United States Patent [19]
Fujita et al.

[11] Patent Number: 5,703,921
[45] Date of Patent: Dec. 30, 1997

[54] X-RAY COMPUTED TOMOGRAPHY APPARATUS

[75] Inventors: Hidehiro Fujita; Hisashi Tachizaki, both of Tochigiken, Japan

[73] Assignee: Kabushiki Kaisha Toshiba, Kawasaki, Japan

[21] Appl. No.: 654,675

[22] Filed: May 29, 1996

[30] Foreign Application Priority Data

May 30, 1995 [JP] Japan ................... P7-131664

[51] Int. Cl.$^6$ ................................ G06F 15/62
[52] U.S. Cl. .................. 378/4; 378/15; 378/19
[58] Field of Search ...................... 378/4, 15, 19, 378/193, 195, 196, 197

[56] References Cited

U.S. PATENT DOCUMENTS

| | | | |
|---|---|---|---|
| 4,112,303 | 9/1978 | Brandt | 378/4 X |
| 4,426,715 | 1/1984 | Baer et al. | 378/4 |
| 4,646,333 | 2/1987 | Yoshida et al. | 378/4 |
| 4,991,190 | 2/1991 | Mori | 378/4 |
| 5,448,608 | 9/1995 | Swain et al. | |

FOREIGN PATENT DOCUMENTS

| | | | |
|---|---|---|---|
| 61-201182 | 9/1986 | Japan | 378/4 |
| 2026812 | 2/1980 | United Kingdom | 378/15 |

*Primary Examiner*—David P. Porta
*Attorney, Agent, or Firm*—Oblon, Spivak, McClelland, Maier & Neustadt, P.C.

[57] ABSTRACT

In an X-ray computed tomography apparatus for producing a sectional image of an object, an X-ray computed tomography gantry comprises an X-ray tube unit, an X-ray tube cooling unit, an X-ray detection unit, a signal amplifier unit, a mechanical control unit, and a power source unit. These units are fixed on the rotating base. These units are integrally fixed at portions thereof opposite to portions thereof fixed on the rotating base by a band.

15 Claims, 12 Drawing Sheets

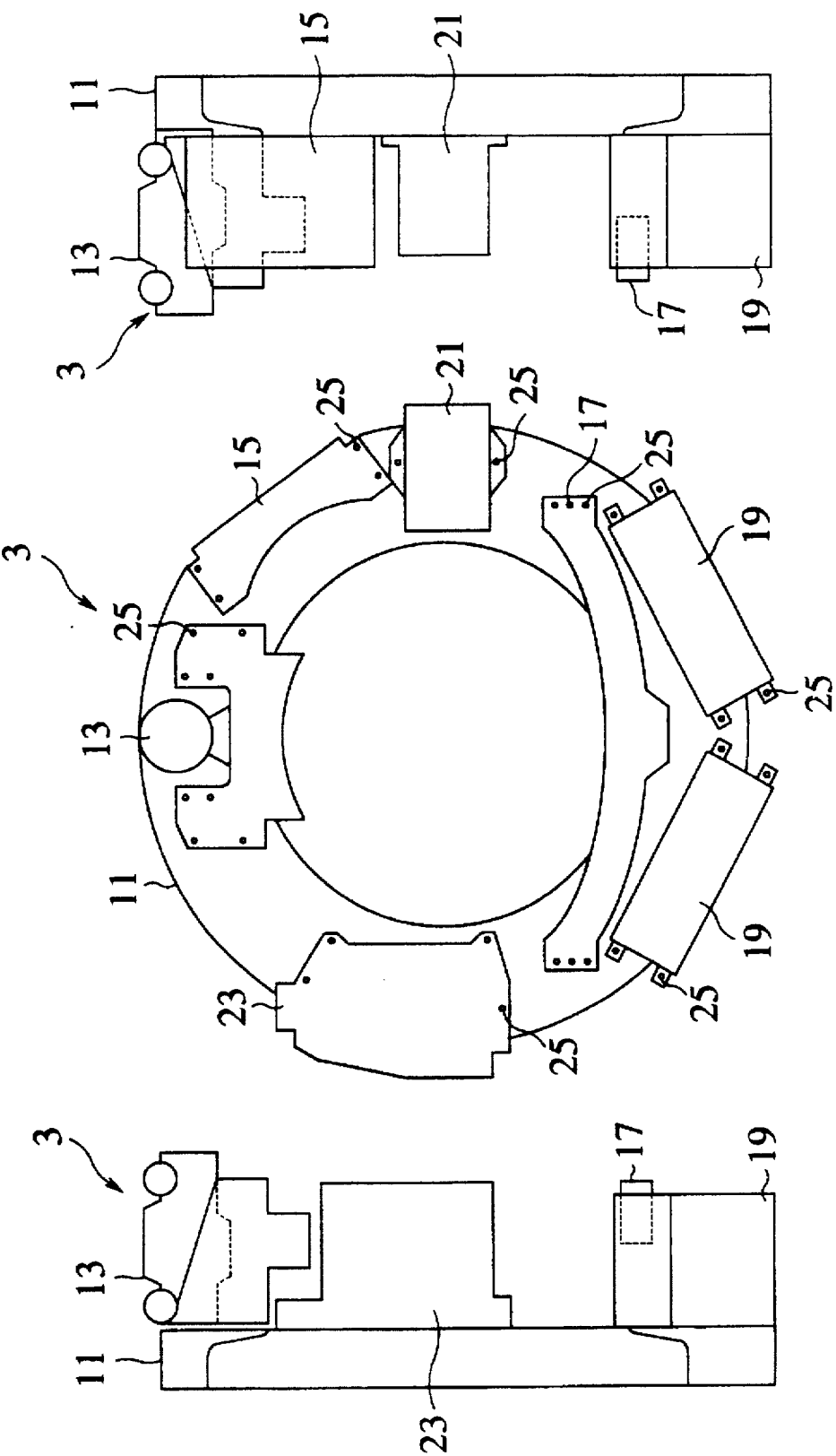

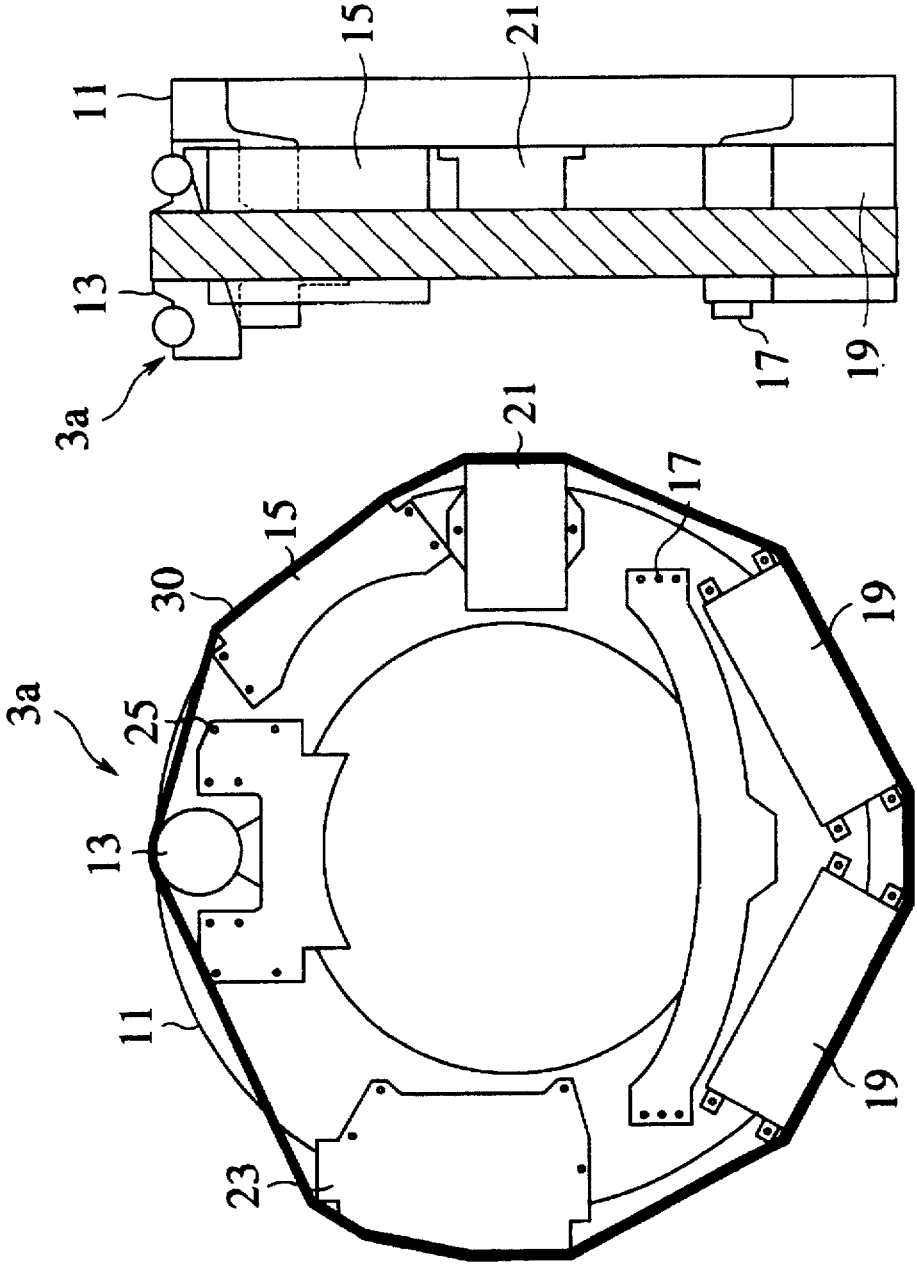

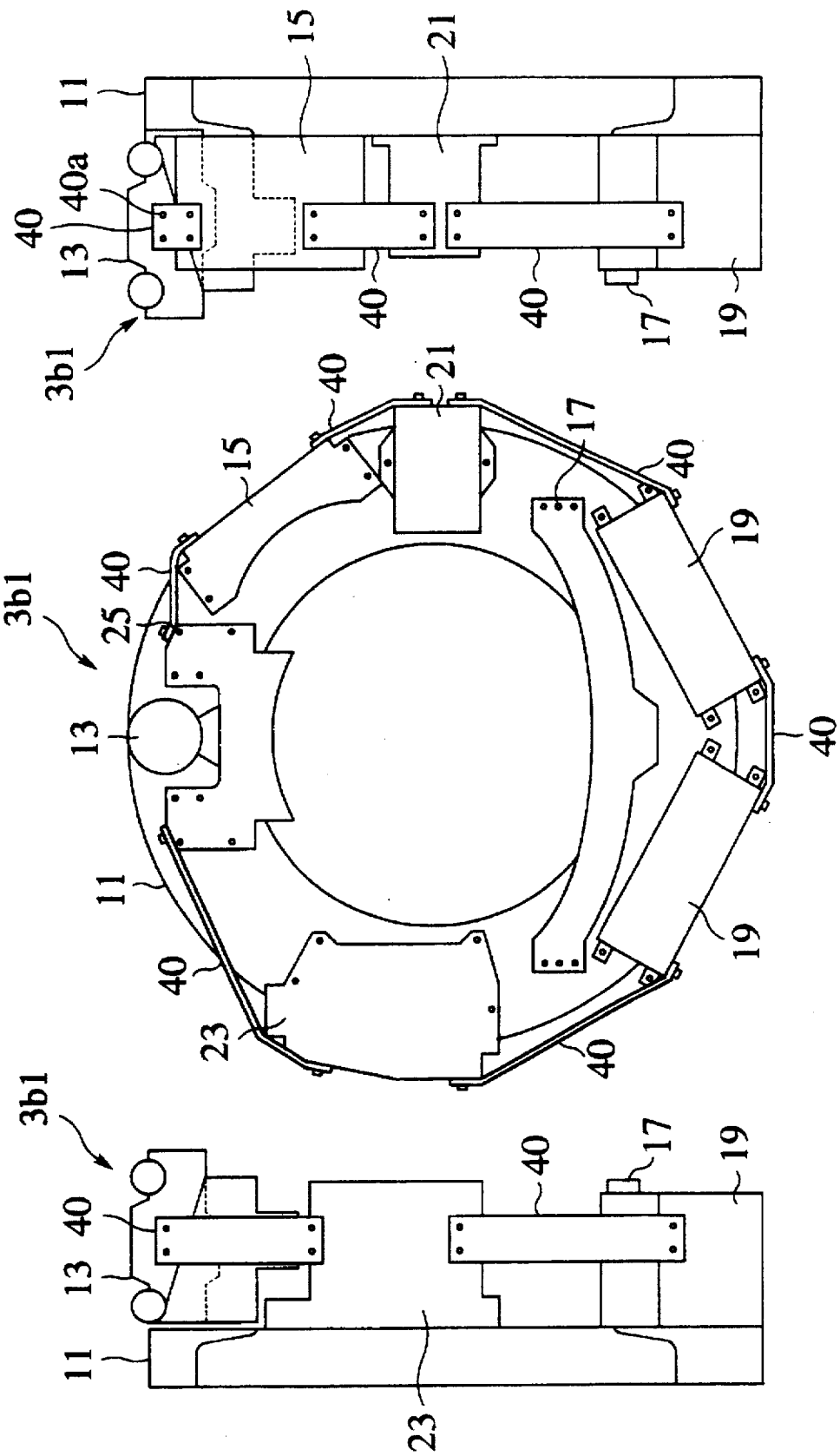

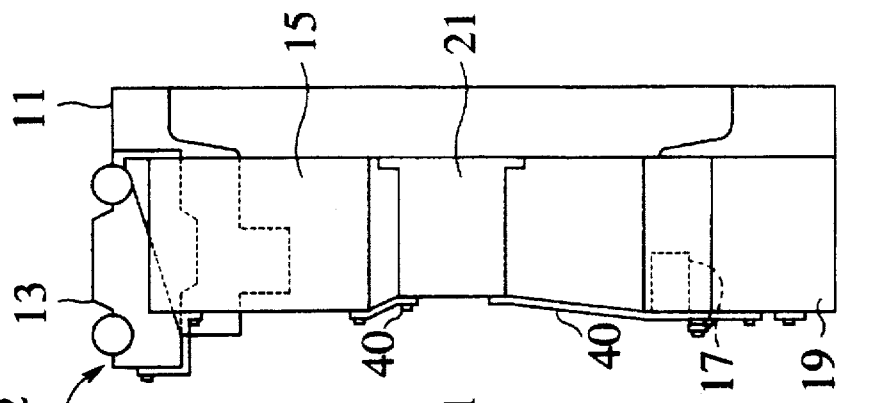
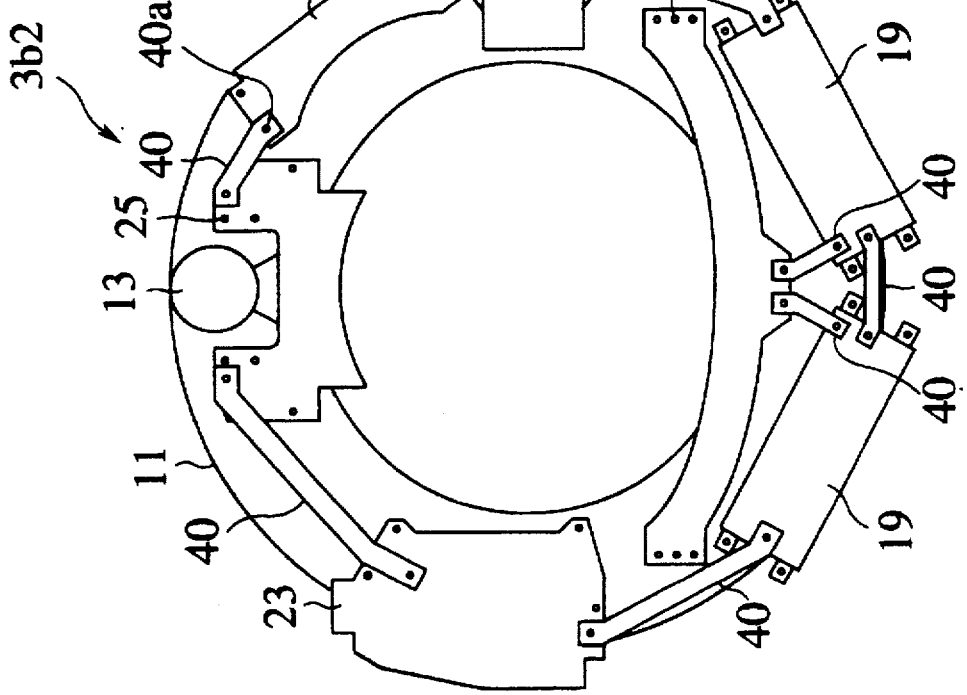
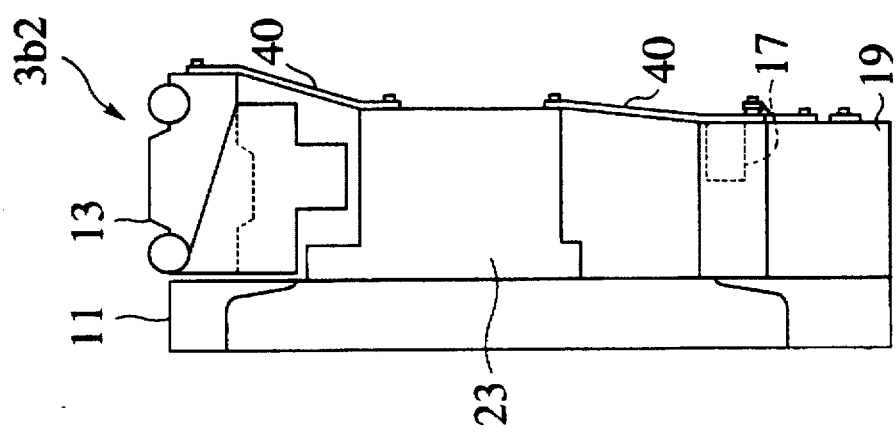

X-RAY COMPUTED TOMOGRAPHY APPARATUS

BACKGROUND OF THE INVENTION

1. Field of the Invention

This invention relates to an X-ray computed tomography apparatus for producing a slice image of an object to be inspected, more particularly to an X-ray computed tomography apparatus having a rotating portion for rotating at a high-speed to obtain a slice image relating to the object.

2. Description of the Prior Art

FIG. 13 shows a conventional X-ray computed tomography (hereinafter called X-ray CT) apparatus 100 comprising an X-ray CT gantry 10 for irradiating X-ray to an object to be inspected to obtain a sectional image signal of the object, a control unit 50 for controlling movements of the X-ray CT gantry 10 and for image processing of the sectional image signal obtained by the X-ray CT gantry 10 to display a processed image signal, and a couch 70 for carrying the object thereon, wherein each cable for connecting a rotating portion with a stationary portion in the X-ray CT gantry 10 is substituted by a slip ring. However, with this apparatus there is a possibility of having errors in signal transmissions due to use of slip rings. To avoid such errors, an apparatus which amplifies the obtained sectional image signal at the rotating side has been developed.

The X-ray CT apparatus 100 which amplifies the sectional image signal has, as shown in FIG. 1, a rotating portion 3 consisting of an X-ray tube unit 13 for irradiating X-ray, an X-ray tube cooling unit 15 for cooling the X-ray tube, an X-ray detection unit 17 for detecting the X-ray irradiated and passed through the object, a signal amplifier unit 19 for amplifying the signal detected by the X-ray detection unit 17, a mechanical control unit 21 for controlling the rotation of the rotating portion 11, and a power source unit 23 for supplying the power to the X-ray tube unit 13, the X-ray tube cooling unit 15, the X-ray detection unit 17, the signal amplifier units 19 and the mechanical control unit 21, and these units are fixed by bolts 25 on a rotating base 11 in the X-ray CT gantry 10.

However, recently, with the X-ray CT apparatus 100 as shown in FIG. 13, it tends to use the apparatus by rotating the rotating portion of the X-ray CT gantry 10 at a high-speed for the purpose of shortening a time of inspection. Particularly, with the X-ray CT apparatus having a high-speed scanning of less than one second per a cycle of one scan, bolts 25 should be made larger and increased these numbers due to an increase of centrifugal force by the high speed rotation. There is a problem that the rotating portion 3 is made larger, consequently, it results in making the X-ray CT apparatus 100 itself larger.

SUMMARY OF THE INVENTION

It is therefore an object of the present invention is to provide an X-ray CT apparatus capable of rotating a rotating portion at a high-speed without making the rotating portion larger.

In accordance with this invention, there is provided an X-ray CT apparatus comprising of an X-ray CT gantry for irradiating X-ray to an object to be inspected for producing a sectional image signal relating to the object. The X-ray CT gantry has a rotating base, a plurality of units fixed on one side of the rotating base, and fixing means for integrally fixing the plurality of units at portions thereof opposite to portions thereof fixed on the rotating base. The X-ray CT apparatus has a control unit for controlling movements of the X-ray CT gantry and for image processing the sectional image signal to display the image, and a couch for carrying the object thereon.

According to this invention, it has more strength of a rotating portion against centrifugal force when rotating the rotating portion, since fixing members are provided for integrally fixing the plurality of units at portions thereof opposite to portions thereof fixed on the rotating base.

According to a preferable embodiment of this invention, the fixing means is a cloth band for tying around the plurality of units. The shape of the cloth band is unchangeable.

According to a preferable embodiment of this invention, the fixing means is a rigid member for fixing the units adjacent to each other.

According to a preferable embodiment of this invention, the fixing means is an annular fixing member. The annular fixing member is fixed on surfaces of the plurality of units opposite to surfaces thereof fixed on the rotating base.

In accordance with this invention, this invention provides the X-ray CT apparatus comprising the X-ray CT gantry having the plurality of units and the rotating base which the units are fixed to. The X-ray CT gantry irradiates X-ray to the object to be inspected for producing the sectional image signal relating to the object. The X-ray CT apparatus has a control units for controlling the movements of the X-ray CT gantry and for image processing the sectional image signal to display the image, and a couch for carrying the object thereon.

According to a preferable embodiment of this invention, the rotating base comprises a disc member and a cylindrical member for covering an outer periphery of the disc member. The plurality of units are fixed in holes provided at adjacent to the outer periphery of the disc member.

According to a preferable embodiment of this invention, the rotating base comprises two annular members arranged parallel each other and a cylindrical member consisting of a plurality of bars for connecting the two annular members.

According to a preferable embodiment of this invention, the rotating base comprises a disc member and a plurality of fixing members which are formed integrally with the disc member for fixing said plurality of units.

In accordance with this invention, this invention provides the X-ray CT apparatus comprising an X-ray CT gantry having the rotating base comprising the disc member and the cylindrical member for covering the outer periphery of the disc member, and having the plurality of units being fixed on one side of the disc member and/or on an inner surface of the cylindrical member. The X-ray CT gantry irradiates X-ray to the object to be inspected and for producing the sectional image signal relating to the object. The X-ray CT apparatus has a control unit for controlling the movements of the X-ray CT gantry and for image processing the sectional image signal to display the image, and a couch for carrying the object thereon.

The nature, principle and utility of the invention will become more apparent from the following detailed description when read in conjunction with the accompanying drawings.

BRIEF DESCRIPTION OF THE DRAWINGS

In the accompanying drawings:

FIGS. 1A, 1B, and 1C are schematic views of a rotating portion in a conventional X-ray CT apparatus;

FIGS. 2A, 2B, and 2C are schematic views of a rotating portion according to a first embodiment of this invention;

FIGS. 3A, 3B, and 3C are schematic views of a rotating portion according to a second embodiment of this invention;

FIGS. 4A, 4B, and 4C are schematic variant views of a rotating portion according to a second embodiment of this invention;

DESCRIPTION OF THE PREFERRED EMBODIMENTS

The preferred embodiment of this invention shall be clearly understood from the following description by referring to accompanying drawings.

Figure 13:
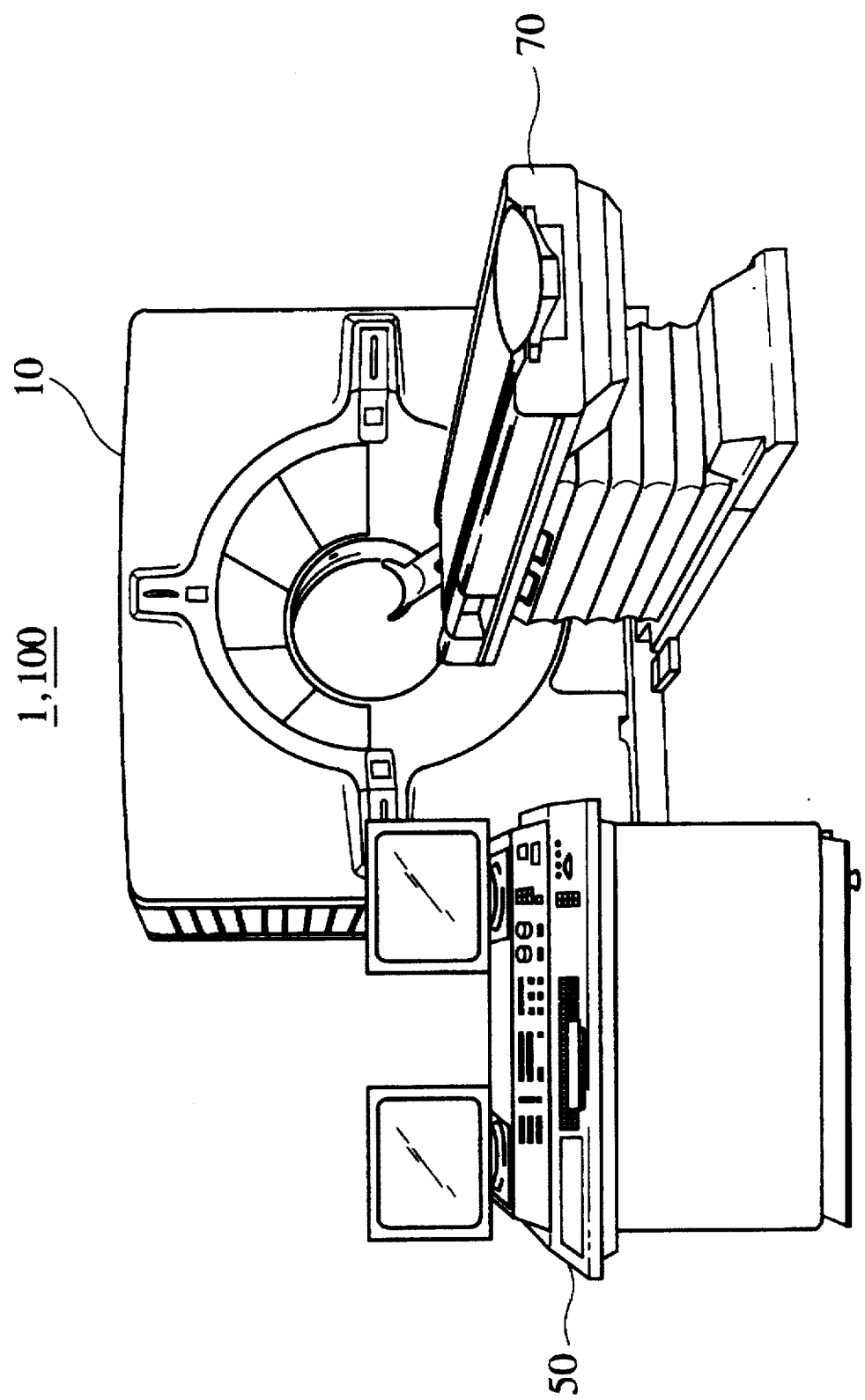
FIG. 13 is a schematic general view of an X-ray CT apparatus.

The entire structure of an X-ray CT apparatus in this invention is substantially the same as a conventional apparatus such as an X-ray CT apparatus 1 as shown in FIG. 13. The X-ray CT apparatus 1 comprises an X-ray CT gantry 10 for irradiating X-ray to an object to be inspected to obtain a sectional image signal relating to the object, a control unit 50 for controlling movements of the X-ray CT gantry 10 and for image processing of the sectional image signal provided by the X-ray CT gantry 10 to display a processed image signal, and a couch 70 for carrying the object thereon. Specifically, the X-ray CT gantry 10 provides a rotating portion for rotating at a high speed.

FIGS. 2A, 2B, and 2C are schematic views of a rotating portion 3a of a first embodiment of this invention, wherein FIG. 2A is a front view of the rotating portion 3a, FIG. 2B is a left side view and FIG. 2C is a right side view.

According to the first embodiment of this invention, as shown in FIGS. 2A, 2B, and 2C, the rotating portion 3a comprises an X-ray tube unit 13, an X-ray tube cooling unit 15, an X-ray detection unit 17, a signal amplifier unit 19, a mechanical control unit 21, and a power source unit 23. These units are fixed by bolts 25 on a rotating base 11 and are tied around by a band 30.

The band 30 may be made of an unshrinkable and inextensible cloth such as an unshrinkable and inextensible nylon band, namely a nylon sling. A metal such as a wire or a steed belt may also be used. Thus, a band of any material may be used as long as its shape remains unchanged.

The band 30 is fastened as follows.

The X-ray tube unit 13, the X-ray tube cooling unit 15, the X-ray detection unit 17, the signal amplifier unit 19, the mechanical control unit 21, and the power source unit 23 are fixed on the rotating base 11 by bolts 25 in the conventional manner.

Subsequently, the band 30 is placed around the plurality of units. Then, the band 30 is tightened so as not to drop from the units, neither the plurality of units drop out of the rotating portion 11. The band 30 is fixed in the same manner by a buckle of a body belt ( pants belt ). As for the fixing member is not limited to the buckle of the body belt, other band fixing member may be used. Further, instead of employing the band fixing member, an adhesive may be used as a fixing member.

As described above, in the X-ray CT apparatus according to the first embodiment, the X-ray CT apparatus comprises the X-ray tube unit 13, the X-ray tube cooling unit 15, the X-ray detection unit 17, the signal amplifier unit 19, the mechanical control unit 21, and the power source unit 23. These units are fixed on the rotating base 11 by bolts 25 and secured by the band 30. When the rotating portion is rotated, centrifugal force between the units diametrically opposing to each other (180° in the opposite direction) is offset. Thus, this structure provides a high-speed rotating portion 3a without making bolts 25 larger, increasing their numbers, consequently, the X-ray CT apparatus 1 itself is prevented from being made larger. The first embodiment has an advantage of providing an easy manufacturing, though a degree of precision of positioning of each unit is not so high as compared with other embodiments.

The description will now proceed to a second embodiment of this invention.

FIGS. 3A, 3B, and 3C are schematic views of a rotating portion 3b1 of the second embodiment of this invention, wherein FIG. 3A is a front view of the rotating portion, FIG. 3B is a left side view, and FIG. 3C is a right side view. The appearance of the X-ray CT apparatus of the second embodiment is substantially the same as that of the first embodiment as shown in FIGS. 2A, 2B, and 2C, and therefore the details are omitted from the drawing and the description.

According to the second embodiment of this invention, as shown in FIGS. 3A, 3B, and 3C, the rotating portion 3b1 comprises the X-ray tube unit 13, the X-ray tube cooling unit 15, the X-ray detection unit 17, the signal amplifier unit 19, the mechanical control unit 21, and the power source unit 23. These units are fixed by bolts 25 on the rotating base 11 and connected adjacent units each other by fixing member 40.

The fixing members 40 are made by rigid body such as metal or ceramics etc., are formed corresponding to the shapes of the plurality of units and distance among the units. Fixing members are connected to the units by fixing-member-bolts 40a. Female screws (not shown) which correspond to fixing-member-bolts 40a are provided at a desirable position on each unit. Fixing members 40 have penetrating holes (not shown) to be penetrated by fixing-member-bolts 40a. In this case, as described above, fixing members 40 are connected to the units by fixing-member-bolts 40a. Besides, a bolt may be projected from each unit. A fixing member 40 may have a perpetration to be penetrated by the bolt and to be fixed from the top of it by a nut.

Further, an adhesive or welding may also be used instead of fixing-member-bolts 40a. The second embodiment provides a higher degree of precision of positioning of each unit and increasing loads for each bolt compared with the first embodiment.

In the case of the rotating portion 3b1 according to the second embodiment as shown in FIG. 3, the fixing member 40 is connected to an outer surface of each unit, but fixing member 40 may be connected to any surface such as an inside surface of each unit or on the surface thereof.

FIGS. 4A, 4B, and 4C are schematic variant views of a rotating portion 3b2 of the second embodiment of this invention, wherein FIG. 4A is a front view of the rotating portion 3b2, FIG. 4C is a right side view, FIG. 4B is a left side view. In this variant case, fixing members 40 are fixed at one opposite side of another side which is fixed to the rotating base of each unit.

Figure 5A:
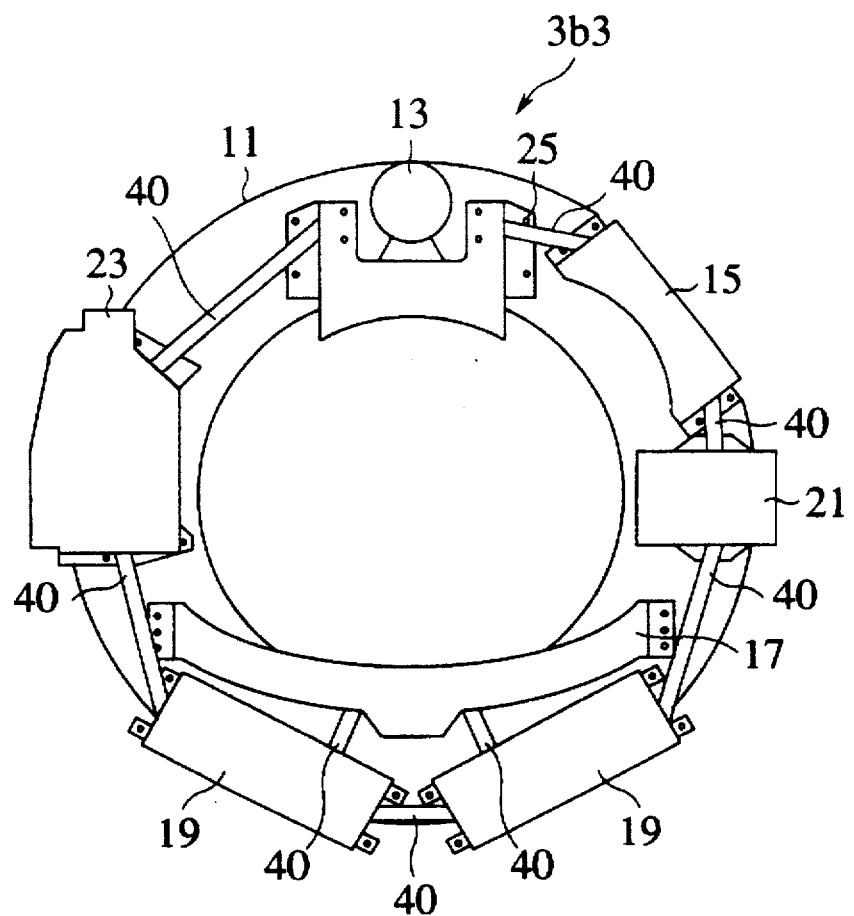
FIG. 5A is another schematic variant view of a rotating portion according to a second embodiment of this invention.
Figure 5B:
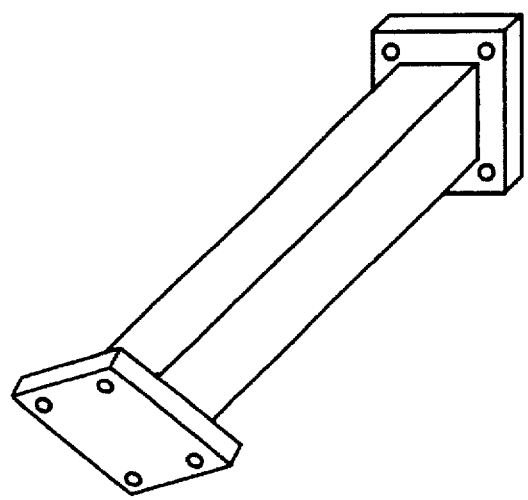
FIG. 5B is a schematic detailed view of a square pipe when used as a fixing member.

FIG. 5A is another schematic variant view of the rotating portion 3b3 according to the second embodiment of this invention. In this variant case, fixing members 40 are connected at the opposite sides of each unit. In this case, a square pipe or a round pipe may be used for a fixing member 40. FIG. 5B is a schematic detailed view of the square pipe when it is used for a fixing member. As shown in the same figure, flange portions are provided at the ends of the pipe, respectively. The square pipes are secured by bolts and the like on each unit. When each square pipe or round pipe used for a fixing member has a higher strength than when used a plate for a fixing member.

According to the second embodiment of this invention, the X-ray CT apparatus comprises the X-ray tube unit 13, the X-ray tube cooling unit 15, the X-ray detection unit 17, the signal amplifier unit 19, the mechanical control unit 21, and the power source unit 23. These units are fixed by bolts 25 on the rotating base 11 and connected to adjacent units by rigid fixing members 40. When the rotating portion 3b is rotated, centrifugal force is distributed to adjacent units each other and offset between the units diametrically opposing to each other (180° in the opposite direction). Thus this structure provides the rotating portion 3b for rotating at a high speed without making bolts 25 larger and increasing their numbers, consequently, the X-ray CT apparatus itself is prevented from being made larger.

The description will now proceed to a third embodiment.

Figure 6:
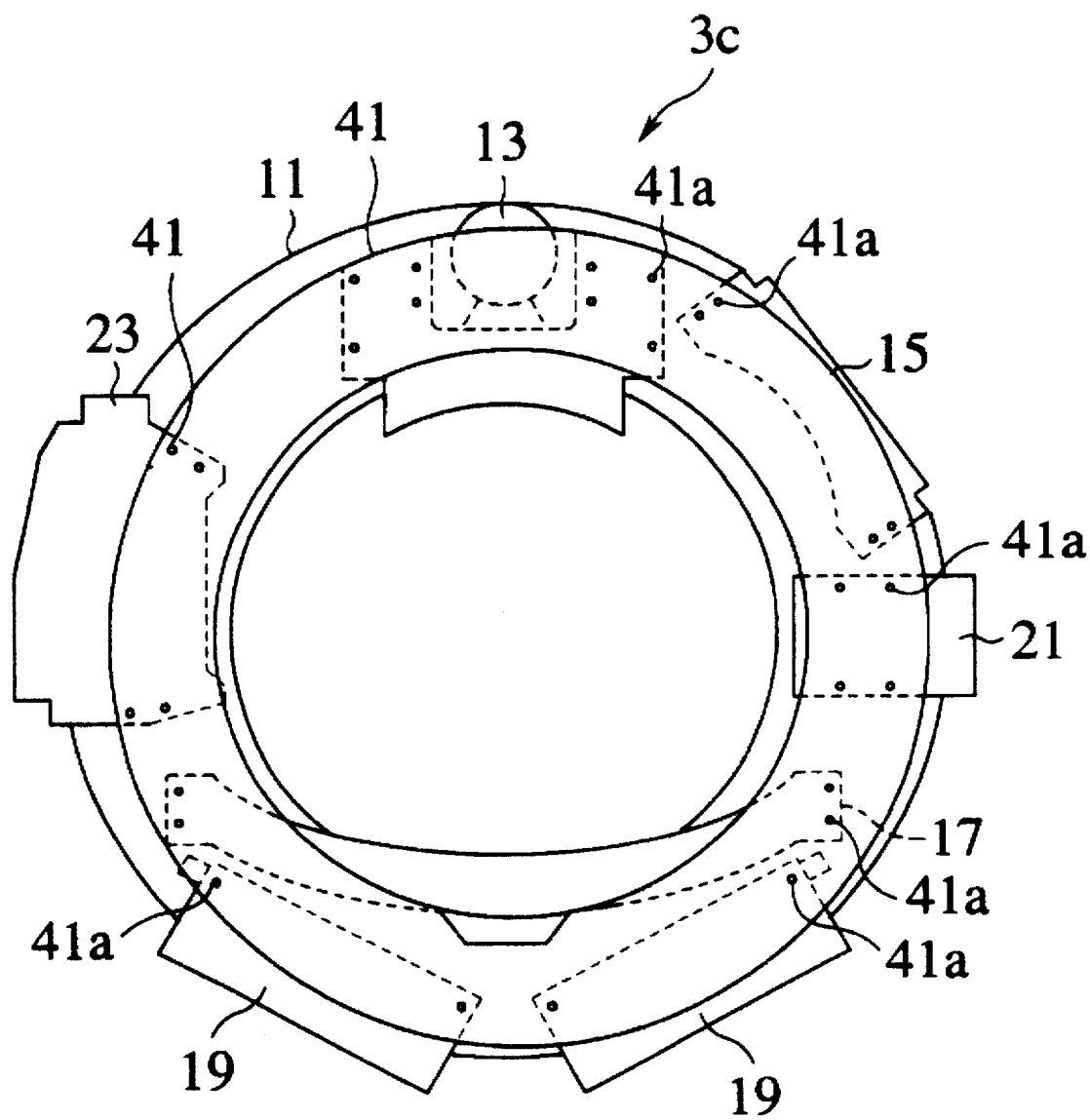
FIG. 6 is a schematic front view of a rotating portion according to a third embodiment of this invention.

FIG. 6 is a schematic front view of a rotating portion 3C according to the third embodiment of this invention. The appearance of the X-ray CT apparatus of the third embodiment is substantially the same as that of the first embodiment as shown in FIGS. 2A, 2B, and 2C, and therefore the details are omitted from the drawing and the description.

As shown in FIG. 6, in the third embodiment, the X-ray CT apparatus comprises the X-ray tube unit 13, the X-ray tube unit 15, the X-ray detection unit 17, the signal amplifier unit 19, the mechanical control unit 21, and the power source unit 23. These units are fixed by bolts 25 on the rotating base 11 and surfaces of the units are connected by annular fixing members 41, respectively.

The annular fixing member 41 is made by rigid body such as metal or ceramics, and formed corresponding to the location of each unit. The height of each unit may be uniformed each other corresponding to the rotating portion 11. An annular fixing member 41 itself may have steps in accordance with the height of each unit.

Annular fixing members 41 are connected to the units by fixing-member-bolts 41a. Female screws (not shown) which correspond to fixing-member-bolts 41a are provided at a desirable position on each unit. Annular fixing members 41 have penetrations holes (not shown) to be penetrated by fixing-member-bolts 41a and are fixed by them. Further, an adhesive or welding may also be used instead of using fixing member-bolts 41a.

In this embodiment, there is an advantage of preventing each unit from moving forward, though an efficiency of maintenance decreases.

in this embodiment, the X-ray CT apparatus comprises the X-ray tube unit 13, the X-ray tube cooling unit 15, the X-ray detection unit 17, the signal amplifier unit 19, the mechanical control unit 21, and the power source unit 23. These are fixed by bolts 25 and secured by annular fixing members 41. When the rotating portion 3c is rotated, centrifugal force is distributed to adjacent units and offset between the units diametrically opposing to each other (180° in the opposite direction). Thus this structure provides the rotating portion 3c for rotating at a high-speed. Bolts 25 which secure each unit are prevented from being made larger.

Figure 7:
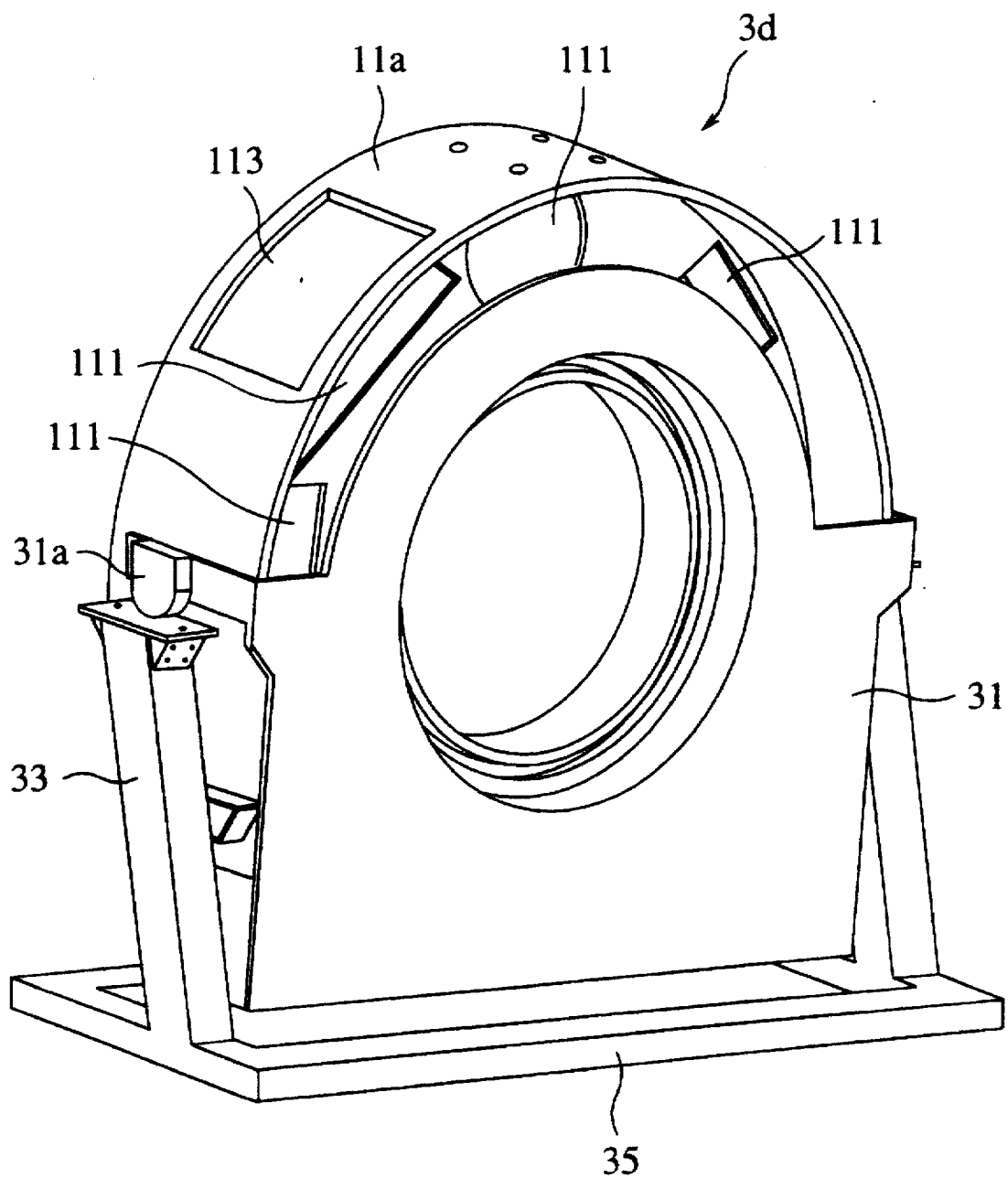
FIG. 7 is a schematic inside view of an X-ray CT gantry according to a fourth embodiment of this invention.
Figure 8:
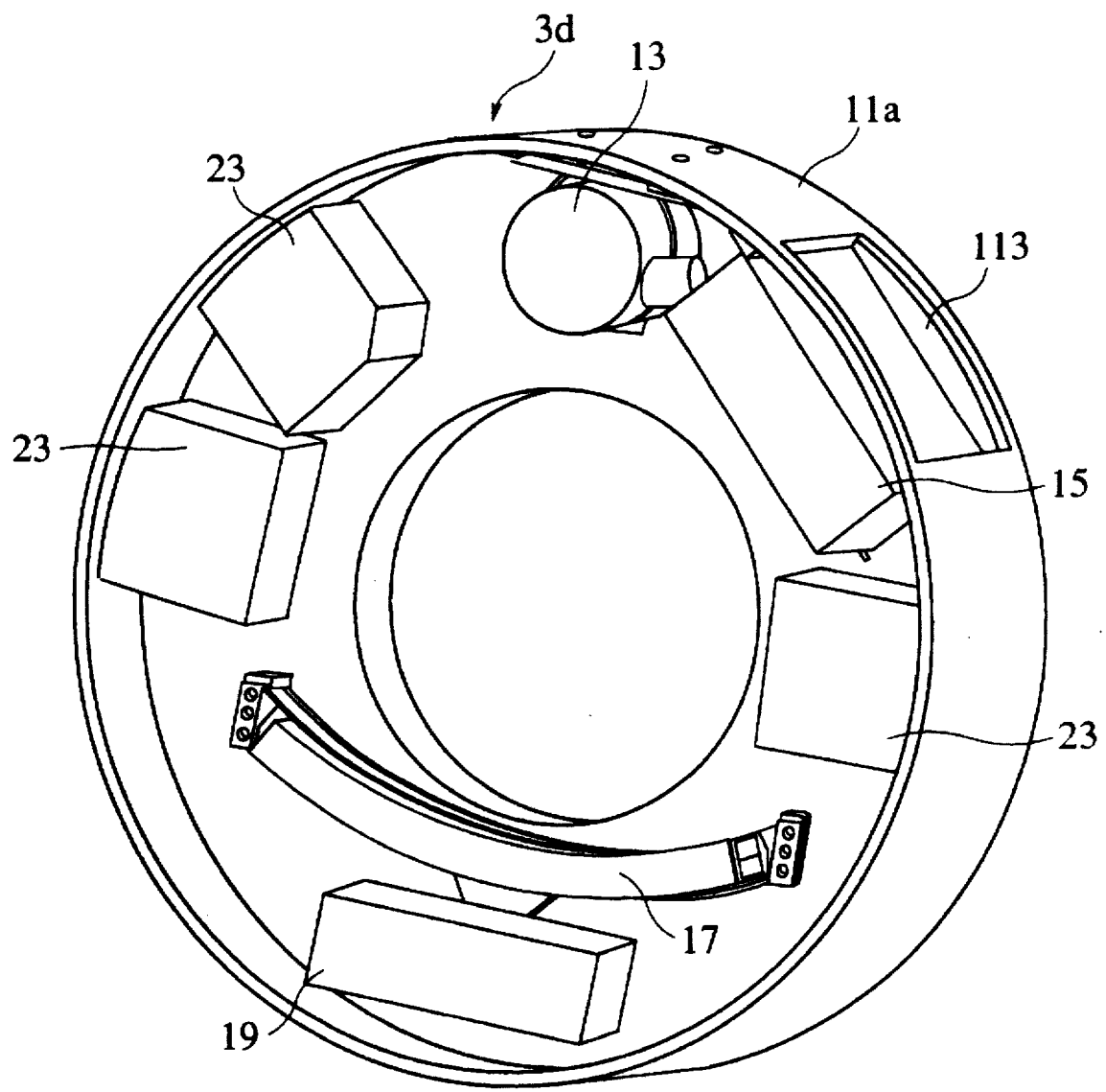
FIG. 8 is a schematic perspective view of a rotating portion in an X-ray CT gantry according to a fourth embodiment of this invention.
Figure 9:
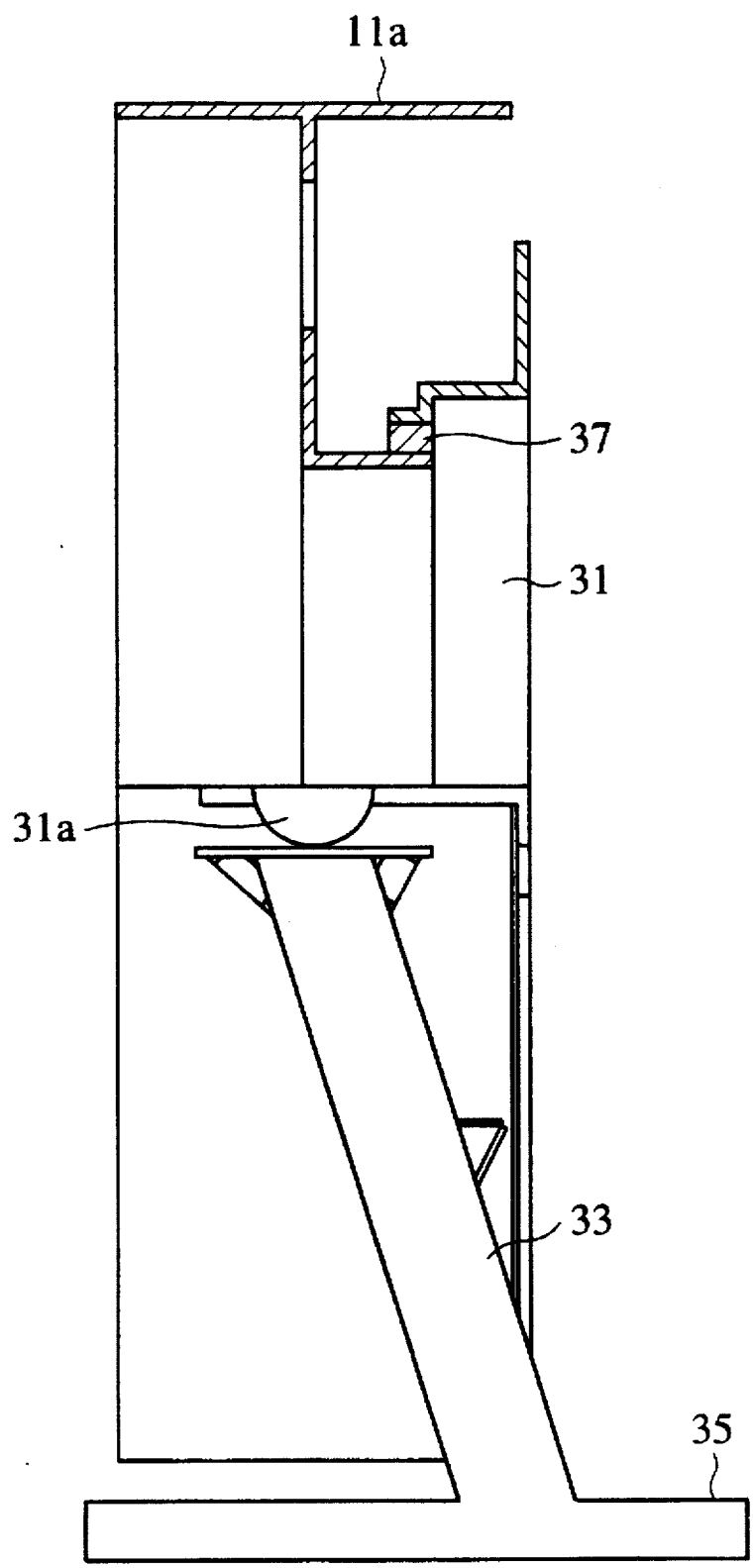
FIG. 9 is a schematic partial sectional view of an X-ray CT gantry of this invention.

FIG. 7 is a schematic view of the internal structure of a fourth embodiment of an X-ray CT gantry 10 of this invention. FIG. 8 is a schematic perspective view of a rotating portion 3d of the X-ray CT gantry 10 according to the fourth embodiment. FIG. 9 is a schematic partial side view of the X-ray CT gantry 10 and a part of section viewed from the side of the rotating portion 3d of the X-ray CT gantry 10. The appearance of the X-ray CT apparatus in the fourth embodiment is substantially the same with that of the first embodiment as shown in FIGS. 2A, 2B, and 2C, and details are, therefore, omitted from the drawing and the description.

The X-ray CT gantry 10 according to the fourth embodiment comprises a rotating portion 3d, a fixing gantry 31, a support 33, and a base 35. The fixing gantry 31 and the rotating portion 3d are supported by the base 35 and the support 33. As shown in FIG. 9, the rotating portion 3d is rotatable with respect to the fixing gantry 31 by means of through the bearing 37. Furthermore, the fixing gantry 31 is capable of tilting against the support 33 by a rotating shaft 31a. Therefore, the rotating portion 3d is also capable of tilting against the support 33.

The detailed description will now proceed to the rotating portion 3d according to the fourth embodiment.

In the fourth embodiment employing the rotating base 11a has a T-shaped section of the circumference. A disc portion on the rotating base 11a having holes 111 corresponding to the plurality of units such as the X-ray tube unit 13, the X-ray tube cooling unit 15, the X-ray detection unit 17, the signal amplifier unit 19, and the power source unit 23, etc., respectively. The rotating base 11b are fixed with the units by the holes 111. In FIG. 9, details of each unit are omitted. The units adjacent to the circumference may be fixed thereto. Furthermore, a hole 113 is for the light weighting and the heat radiation of the rotating base 11a.

According to the fourth embodiment, the holes on the disc of the rotating base 11a fix the X-ray tube unit 13, the X-ray tube cooling unit 15, the X-ray detection unit 17, the signal amplifier unit 19, and the power source unit 23, etc. The center of gravity is supported at an internal surface of the holes. The inner surface receives on centrifugal force without concentrating centrifugal force at one point such as the screw which supports each unit in the first, second, and third embodiments. Thus, each unit can be securely supported, and problem of concentration of centrifugal force to the screw portion is resolved. Consequently, the durability of providing units is improved. In the variation of the fourth embodiment, it is preferable that the rotating base 11a has a section of the L-shaped circumference thereof. In the case, an inner surface of a rotating base 11b and/or one side of the disc portion are/is for fixing the plurality of units comprising such as the X-ray tube unit, the X-ray tube cooling unit, the X-ray detection unit, the signal amplifier unit, and the power source unit etc.

A stand 115 as shown in FIG. 8 is provided to a position of which the units in the inner surface of the 11b is fixed so as that a fixing surface opposite to inner surface of the units in close contact of the inner surface of the unit, and fixed by fixing bolts. The unit may be fixed directly to the inner surface of the rotating base 11 instead of providing the stand 115.

Furthermore, in the case of an arrangement of the X-ray detection unit is not located in the inner surface of the rotating base 11b, the stand 115 may be extended from the inner surface of the rotating base 11b to fix the units.

Figure 10:
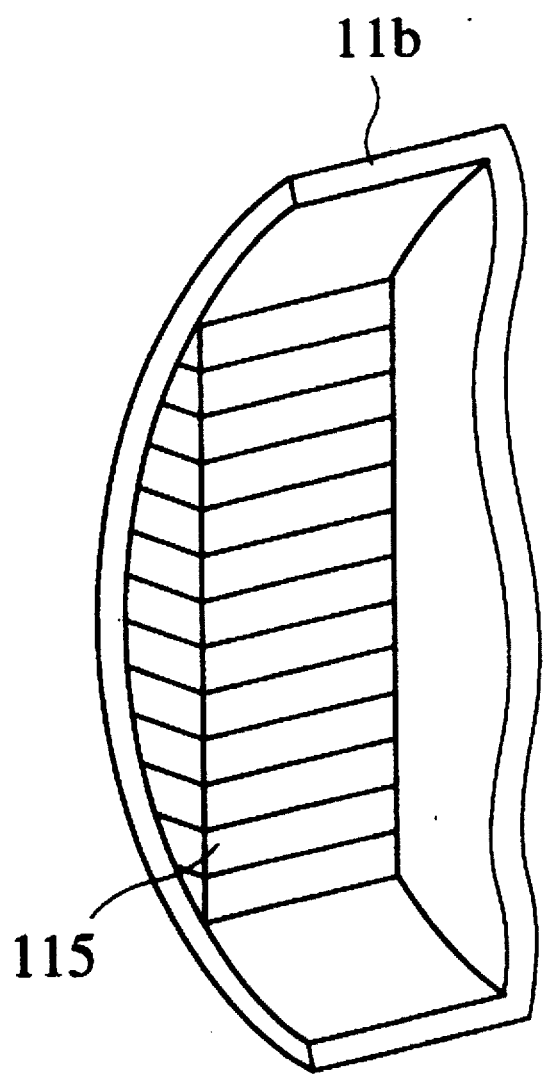
FIG. 10 is a schematic view of a stand provided for a variant rotating portion according to fourth embodiment of this invention.
Figure 11:
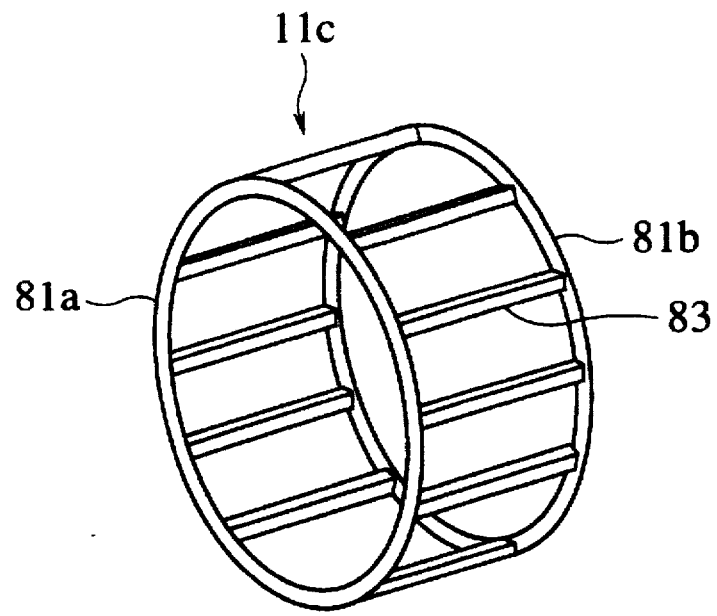
FIG. 11 is a schematic view of a variant rotating base according to a fourth embodiment of this invention.

According to the embodiments shown in FIG. 7 and FIG. 10, a cylindrical rotating bases 11a, 11b are employed, however a rotating base having a shape of cylinder may be employed, wherein the rotating base comprises two annular members 81a, 81b disposed parallel each other and a plurality of bars 83 for connecting the two annular members 81a, 81b as shown in FIG. 11. In this case, the stand 115 is provided inside at least two bars 83. However, each unit may be fixed directly to the bars 83 without providing the stand 115. The rotating base 11c as described above has an advantage of the light weighting of a whole apparatus and easily releasing the produced heat.

Figure 12:
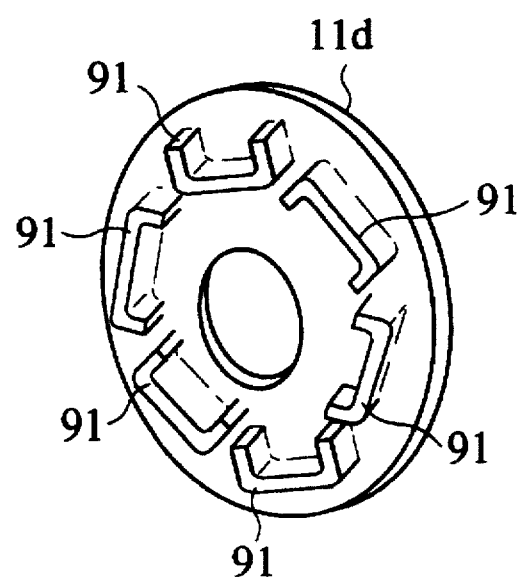
FIG. 12 is a schematic plan view of a rotating base according to a fifth embodiment of this invention.

FIG. 12 is a schematic plain view of a rotating base 11d disposed in an X-ray CT apparatus according to a fifth embodiment of this invention. The appearance of the X-ray CT apparatus in the fifth embodiment is substantially the same with that of the first embodiment as shown in FIGS. 2A, 2B, and 2C, and therefore details are omitted from the drawing and the description.

According to the fifth embodiment as shown in FIG. 12, the X-ray CT apparatus comprises the rotating base 11d integrally formed with a plurality of unit fixing members 91 for fixing the X-ray tube unit 13, the X-ray tube cooling unit 15, the X-ray detection unit 17, the signal amplifier unit 19, the mechanical control unit 21, and the power source unit 23. The units are fixed by the unit fixing member 91 disposed on the rotating base 11d.

The fixing members 91 for fixing the units comprises plates each having substantially a U-shaped cross section and corresponding to the size of each unit. The units are fixed to the corresponding fixing members 91 by bolts.

As described above, the X-ray CT apparatus according to the fifth embodiment comprises the rotating base 11d integrally formed with the fixing member 91 for fixing the X-ray tube unit 13, the X-ray cooling unit 15, the X-ray detection unit 17, the signal amplifier unit 19, the mechanical control unit 21, and the power source unit 23. Thus, the rotating portion has an increase durability against centrifugal force when the rotating portion is rotating, and a high-speed rotation of the rotating portion is , therefore, possible without making it larger.

As described above, the X-ray CT apparatus has a fixing means such as a band for integrally fixing the plurality of units at the portions thereof opposite to another portions which are disposed on the rotating base 11d. Consequently, even if the rotating portion rotate at high speed, strength of the rotating base increases against centrifugal force. In addition, the rotating base itself is so structured to support each unit against centrifugal force, thereby the strength of the rotating base is improved.

It should be understood that many modifications and adaptations of the invention will become apparent to those skilled in the art and it is intended to encompass such obvious modifications and changes in the scope of the claims appended hereto.

What is claimed is:

1. An X-ray computed tomography apparatus comprising:
   an X-ray computed tomography gantry for irradiating X-ray to an object to be inspected and for producing a sectional image signal relating to said object, said X-ray computed tomography gantry comprising a rotating base having a shape of disc, a plurality of units fixed on one side of said rotating base for processing X-ray, and fixing means for integrally fixing said plurality of units at portions thereof apart from portions thereof fixed on said rotating base;
   control means for controlling movements of said X-ray computed tomography gantry and for image processing said sectional image signal to display the image; and
   a couch for carrying said object thereon.

2. An X-ray computed tomography apparatus as claimed in claim 1, wherein said fixing means comprises a cloth band for tying around said plurality of units, said cloth band having unchangeable shape.

3. An X-ray computed tomography apparatus as claimed in claim 1, wherein said fixing means comprises a rigid fixing member for fixing said units adjacent to each other.

4. An X-ray computed tomography apparatus as claimed in claim 3, wherein said fixing means secures said adjacent units at outer periphery thereof.

5. An X-ray computed tomography apparatus as claimed in claim 3, wherein said fixing means secures said adjacent units on surfaces thereof opposite to surfaces thereof fixed on said rotating base.

6. An X-ray computed tomography apparatus as claimed in claim 3, wherein each unit is fixed diametrically opposite to the other units, respectively.

7. An X-ray computed tomography apparatus as claimed in claim 1, wherein said fixing means comprises an annular fixing member disposed on surfaces of said plurality of units opposite to surfaces thereof fixed on said rotating base.

8. An X-ray computed tomography apparatus as claimed in claim 1, wherein said apparatus has a scanning cycle of less than one second per a cycle of one scan.

9. An X-ray computed tomography apparatus comprising:
   an X-ray computed tomography gantry for irradiating X-ray to an object to be inspected for producing a sectional image signal relating to said object, said X-ray computed tomography gantry having a plurality of units and a rotating base for fixing said plurality of units thereto, said rotating base having a disc member and a cylindrical member for covering an outer periphery of said disc member, and said plurality of units being fixed into holes formed on said disc member near the outer periphery thereof;
   controlling means for controlling movements of said X-ray computed tomography gantry and for image processing said sectional image signal to display the image; and
   a couch for carrying said object thereon.

10. An X-ray computed tomography apparatus as claimed in claim 9, wherein said X-ray computed tomography gantry further comprises a fixing gantry and a bearing, which is fixed on said fixing gantry, for rotatably supporting said rotating member on an inner diameter portion thereof.

11. An X-ray computed tomography apparatus as claimed in claim 9, wherein said cylindrical member comprises a hole for lightening and radiating heat.

12. An X-ray computed tomography apparatus as claimed in claim 10, wherein said cylindrical member comprises a hole for lightening and radiating heat.

13. An X-ray computed tomography apparatus comprising:

an X-ray computed tomography gantry for irradiating X-ray to an object to be inspected for producing a sectional image signal relating to said object, said X-ray computed tomography gantry having a plurality of units and a rotating base for fixing said plurality of units thereto, said rotating base having a disc member and a plurality of fixing members formed integrally with said disc member for fixing said plurality of units;

controlling means for controlling movements of said X-ray computed tomography gantry and for image processing said sectional image signal to display the image; and a couch for carrying said object thereon.

14. An X-ray computed tomography apparatus comprising:

an X-ray computed tomography gantry for irradiating X-ray to an object to be inspected and for producing a sectional image signal relating to said object, said X-ray computed tomography gantry having a rotating base comprising a disc member and a cylindrical member for covering the outer periphery of said disc member, and having a plurality of units being fixed on one side of said disc member and/or on an inner surface of said cylindrical member;

controlling means for controlling movements of said X-ray computed tomography gantry and for processing said sectional image signal to display an image; and a couch for carrying said object thereon.

15. An X-ray computed tomography apparatus as claimed in claim 14, wherein a stand is provided at a position of cylindrical member to which said unit is fixed, in such manner that a surface of said stand fixed on the inner surface of said cylindrical member is in close contact with the inner surface.

* * * * *